United States Patent [19]

Rossignol

[11] Patent Number: 5,968,961
[45] Date of Patent: *Oct. 19, 1999

[54] PHARMACEUTICAL COMPOSITIONS OF TIZOXANIDE AND NITAZOXANIDE

[75] Inventor: Jean-François Rossignol, Clearwater, Fla.

[73] Assignee: Romark Laboratories, L.C., Tampa, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/852,447

[22] Filed: May 7, 1997

[51] Int. Cl.⁶ .................................................. A61K 31/425
[52] U.S. Cl. ............................................ 514/371; 548/192
[58] Field of Search ............................... 514/371; 548/192

[56] References Cited

U.S. PATENT DOCUMENTS

| | | | |
|---|---|---|---|
| 3,950,351 | 4/1976 | Rossignol et al. | 260/306.8 R |
| 4,315,018 | 2/1982 | Rossignol | 424/270 |
| 5,387,598 | 2/1995 | Rossignol | 514/371 |
| 5,578,621 | 11/1996 | Rossignol | 514/371 |

*Primary Examiner*—Laura L. Stockton
*Attorney, Agent, or Firm*—Pendorf & Cutliff

[57] ABSTRACT

The present invention relates to a pharmaceutical composition containing as active agent, solid particles of a compound selected from the group consisting of:
compound of formula I compound of formula I

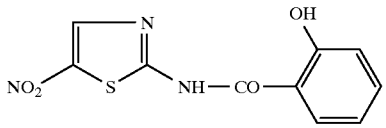

compound of formula II

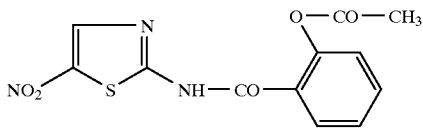

and mixtures thereof,
said particles having a particle size smaller than 200 μm, the mean particle size of the said active solid particles being greater than 10 μm.

It also relates to a pharmaceutical composition which contains at least one pharmaceutically acceptable acid.

44 Claims, 1 Drawing Sheet

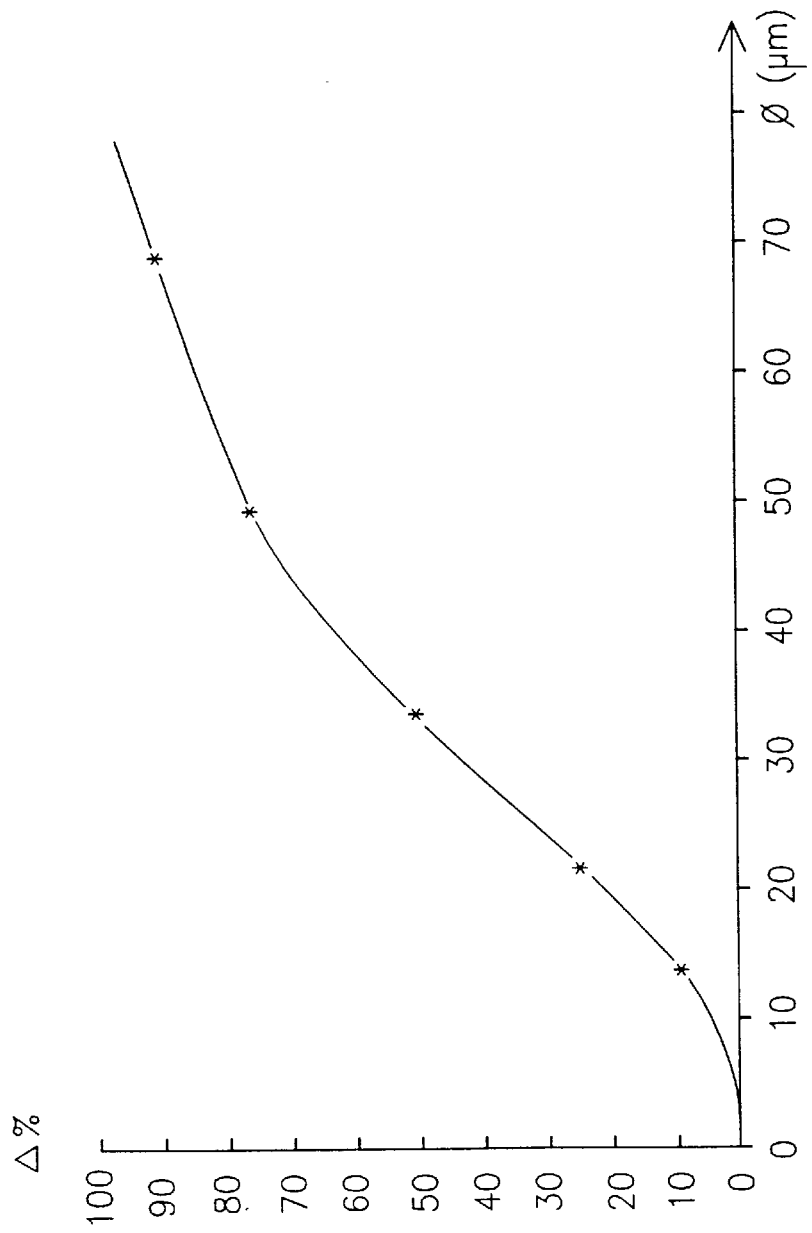

PHARMACEUTICAL COMPOSITIONS OF TIZOXANIDE AND NITAZOXANIDE

THE PRIOR ART

Nitrothiazole compound PH 5776 (2-acetolyloxy)-N-(5-nitro-2-thiazolyl) benzamide) is a compound of formula II

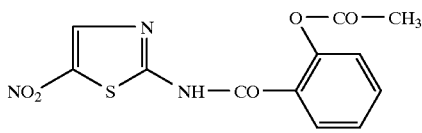

The preparation and uses of this compound are disclosed in U.S. Pat. No. 3,950,351, as well as in publications made by Applicant.

In U.S. Pat. No. 3,950,351, the compound of formula II is prepared by reacting

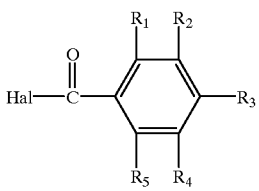

Hal = halide with

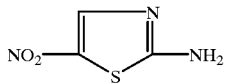

This reaction is not suitable for the preparation of pure compound of formula I.

In WO 95/28393, applicant discloses a method for the manufacture of pure compound of formula I, as well as the use of the composition containing a mixture of compounds of formula I and II.

It has been shown that compound of formula I is effective against parasites, bacteria, fungi and viruses although it does not contain an acyloxy group.

Now, it has now been observed in animal studies and in human clinical studies, that the efficacy of a treatment, using the compounds of formula I and II as prepared by the methods disclosed in said publications, is dependent upon the particle size of the active drug substance and the stability of the compounds.

The aim of the present invention is a pharmaceutical composition which is consistently and optimally effective against parasites, bacteria, fungi and viruses in animals and humans.

Another aim of the present invention is a pharmaceutical composition that maintains its stability after six months or more of storage.

BRIEF DESCRIPTION OF THE INVENTION

The present invention relates to a pharmaceutical composition for oral administration, as a solid dosage form, a liquid suspension, or a paste, and also to a pharmaceutical composition for topical or intravaginal application as a paste, ointment or cream.

The composition of the invention contains an effective amount of solid particles having a particle size smaller than 200 $\mu$m of a compound selected from the group consisting of:

compound of formula I

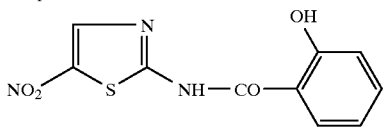

compound of formula II

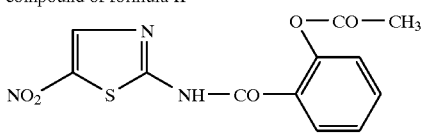

and mixtures thereof, in which the mean particle size of the said active solid particles having a particle size smaller than 200 $\mu$m being greater than 10 $\mu$m. Hereafter in the present specification, the wording "the said active agent" means particles of compound of formula I, compound of formula II and mixtures thereof, the said particles having a particle size smaller than 200 $\mu$m, the means particle size of the said active solid particles being greater than 10 $\mu$m.

For purposes of the present specification, the range of particle sizes of samples of compound of formula I and compound of formula II and the mean particle size of samples of compound of formula I and compound of formula II shall be those determined by a COULTER® Counter LS 100. This equipment uses laser light at 750 nm to size particles from 0.4 to 900 $\mu$m in diameter by light diffraction. The samples are measured in water with a small amount of Triton X-100 in order to increase the wettability and deflocculate the powder.

It has been observed that solid particles of compound of Formula I, compound of Formula II, or mixtures thereof having a particle size between 170 and 520 $\mu$m (means particle size=352 $\mu$m) have a limited efficacy when administered orally to animals or humans.

It has also been observed in dogs that the oral administration of a single dose of 50 milligrams per kilogram of solid particles of compound of Formula I and compound of Formula II having a particle size smaller than 5 $\mu$m, caused severe adverse reactions in the animals.

It has now been discovered that in order to have a very effective and safe treatment of infections caused by parasites, bacteria, fungi and viruses in humans and animals, the pharmaceutical composition, either a solid dosage form or an aqueous suspension must contain the effective dose of the active agent in the form of solid particles having a particle size smaller than 200 $\mu$m and containing compound of formula I and/or compound of formula II, the mean particle size of the said active solid particles being greater than 10 $\mu$m.

The composition of the invention possibly contains particles of compound of formula I and/or compound of formula II with a size larger than 200 $\mu$m. However, the presence of a high content of such particles having a size larger than 200 $\mu$m with respect to the content of particles having a size between 5 and 200 $\mu$m significantly reduces the chemotherapeutic activity of the composition. Preferably, the pharmaceutical compositions of the invention do not contain more than 5% of solid particles of compound of formula I and/or compound of formula II having a size larger than 200 $\mu$m. Most preferably, the pharmaceutical compositions of the invention contain substantially no solid particles of compound of formula I and/or compound of formula II having a size larger than 200 μm.

The composition possibly contains particles of compound of formula I and/or compound of formula II with a size less than 5 μm. The presence of a high content of particles of compound of formula I and/or compound of formula II having a size less than 5 μm with respect to the content of particles having a size between 5 and 200 μm can produce adverse effects in animals or in humans. In addition, it has been observed that particles having a size less than 5 μm are more rapidly absorbed form the gastro-intestinal tract into the bloodstream, and therefore are not as effective against parasites, bacteria, fungi and viruses which commonly live within the gastro-intestinal tract of animals and humans. Preferably, the pharmaceutical compositions of the invention do not contain more than 10% of solid particles of compound of formula I and/or compound of formula II having a size less than 5 μm. Most preferably, the pharmaceutical compositions of the invention contain substantially no solid particles of compound of formula I and/or compound of formula II having a size less than 5 μm.

The skilled scientist could not predict that the particle size of compound of Formula I and compound of Formula II would have such a significant impact upon its antimicrobial activity in animals and in humans. For example, in studies conducted by the Inventor, anti-parasitic compounds such as albendazole, mebendazole, niclosamide, praziquantel and metronidazole have not demonstrated such a marked difference in anti-parasitic activity in animals or humans which was dependent upon their particle size. In addition, a skilled scientist could not predict that particle sizes of compound of Formula I and compound of Formula II would have such an adverse impact upon the ability of animals or humans to tolerate the administration of said active agent.

Advantageously, the mean particle size of the said active solid particles is between 10 and 100 μm, preferably between 20 and 50 μm. Examples of preferred compositions are:

a composition for which less than 10% of the said active solid particles has a particle size larger than 100 μm;

a composition for which at least 50% of the said active solid particles has a particle size smaller than 50 μm.

In accordance with a preferred embodiment of the composition, less than 10% of the said active solid particles has a particle size smaller than 5 μm.

Advantageously, in order to have excellent efficacy against a broad spectrum of parasites, bacteria, fungi and viruses, the distribution factor of the said active solid particles is between 0.8 and 2, preferably between 1.1 and 1.9, most preferably greater than 1.5, said distribution factor being calculated by the following formula:

$$F_{90\%}=(\emptyset_{90\%}-\emptyset_{10\%})/((\emptyset_{90\%}+\emptyset_{10\%})/2)$$

in which $F_{90\%}$ is the distribution factor at 90%;

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

The invention also relates to pharmaceutical compositions described above which contain advantageously at least one pharmaceutically acceptable acid. Examples of such acids are: citric acid, glutamic acid, succinic acid, ethanesulfonic acid, acetic acid, tartric acid, ascorbic acid, methanesulfonic acid, fumaric acid, adipic acid, malic acid and mixtures thereof. Citric acid is very appropriate. The presence of said acid improves the stability of the active agent or agents.

The ratio of the weight of pharmaceutically acceptable acid/the weight of said active solid particles is advantageously between 0.01 and 0.5, preferably between 0.03 and 0.2. Advantageously, the amount of acid is sufficient for adjusting the pH of the suspension between 2 and 6, preferably between 3 and 5, most preferably between 3.5 and 4.5.

The active agent or agents used in the solid dosage form or suspension is advantageously a mixture of solid particles of compounds of formula I and of formula II with a particle size smaller than 200 μm, the weight content of compound of formula II with respect to the weight of compounds of Formula I and of Formula II of said mixture being comprised between 0.5 and 20%, preferably between 0.5 and 10%.

According to a specific embodiment of the invention, active particles of compound of formula I and compound of formula II are prepared by the methods described hereabove and are then milled so that less than 10% of said active particles are larger than 100 μm, less than 50% of said particles are larger than 50 μm and less than 10% of said active particles are smaller than 5 μm in size, the mean particle size being between 20 and 590 μm. Said active particles are then granulated using a mixture containing active solid particles and at least one granulating agent. Examples of granulating agent are: polyvinylpyrrolidone, water, alcohol, sucrose hydroxyl cellulose and mixture thereof. Advantageously, at least one pharmaceutically acceptable acid is added during the granulation process.

The invention relates to solid dosage forms containing a composition of the invention such as tablets, dispersible tablets, coated tablets, matrixes, etc. The dosage form of the invention contains, for example:

solid active particles with a particle size smaller than 200 μm, less than 10% of said particles having a size larger than 100 μm, less than 50% of said particles having a size larger than 50 μm and less than 10% of said particles having a size less than 5 μm, the means particle size being between 20 and 50 μm.

at least one granulating agent;

at least one wetting agent;

at least one starch derivative, and at least one pharmaceutically acceptable acid which is preferably added during the granulation process.

Liquid dosage forms such as aqueous suspensions of the invention contain, for example:

as active agent, solid particles containing a compound of formula I and/or a compound of formula II having a particle size smaller than 200 μm, less than 10% of said particles having a size larger than 100 μm, less than 50% of said particles having a size larger than 50 μm and less than 10% of said particles having a size less than 5 μm, and at least one granulating agent;

at least one wetting agent;

at least one pharmaceutically acceptable acid, the pH of the suspension being between 2 and 6, preferably between 3 and 5, most preferably between 3.5 and 4.5;

at least one thickener, for example a Xanthan gum, a guar gum, crystalline cellulose, carruba gum, carboxymethylcellulose or a mixture thereof.

Paste or ointment forms of the invention suitable for oral administration contain, for example:

as active agent, solid particles containing a compound of formula I and/or a compound of formula II having a particle size smaller than b 200μm, less than 10% of said particles having a size larger than 100 μm, less than 50% of said particles having a size larger than 50 μm and less than 10% of said particles having a size less than 5 μm, and at least one wetting agent;

at least one pharmaceutically acceptable acid, the pH of the suspension being between 2 and 6, preferably between 3 and 5, most preferably between 3.5 and 4.5;

at least one thickener, for example a Xanthan gum, a guar gum, crystalline cellulose, carruba gum, carboxymethylcellulose or a mixture thereof.

Paste or ointment forms for topical or intravaginal application contain, for example:

as active agent, solid particles containing a compound of formula I and/or a compound of formula II having a particle size smaller than 200 μm, less than 10% of said particles having a size larger than 100 μm, less than 50% of said particles having a size larger than 50 μm and less than 10% of said particles having a size less than 5 μm, and at least one wetting agent;

at least one pharmaceutically acceptable acid, the pH of the suspension being between 2 and 6, preferably between 3 and 5, most preferably between 3.5 and 4.5;

cetylic alcohol and/or glyceride derivatives and/or propyleneglycol;

at least one thickener, for example a Xanthan gum, a guar gum, crystalline cellulose, carruba gum, carboxymethylcellulose or a mixture thereof.

Such pharmaceutical compositions, either as solid or liquid dosage forms or as pastes or ointments, can possible contain additional active agents such an antibiotics, antiviral agents or proton pump inhibitors. While it is not advantageous, it is also possible that such pharmaceutical formulations may contain solid particles of compound of Formula I and/or compound of Formula II which are larger than 200 μm.

The pharmaceutical compositions described are suitable for treating human and animal infections caused by parasites, bacteria, fungi and viruses.

BRIEF DESCRIPTION OF THE DRAWING

FIG. 1 shows the percentage of active particles having a size smaller than Øμm.

DESCRIPTION OF EXAMPLES OF PHARMACEUTICAL COMPOSITIONS

Dry pure compound of formula I (desacetyl-nitazoxanide) and dry pure compound of formula II (Nitazoxanide) were submitted to a grinding and sized by means of a mesh screen.

After grinding, the particles of compound of formula I, of formula II and mixtures thereof had the particle size distribution as given in FIG. 1. Said FIG. 1 shows the percentage of particles having a size smaller than Øμm.

From said figure, it appears that:

less than 10% of the particles had a particle size smaller than approximately 5 μm;

less than 10% of the particles had a particle size larger than approximately 70 μm;

the mean particle size is approximately 40 μm;

the distribution factor of the particles is about 1.73, said distribution factor being calculated by the following formula:

$$F_{90\%} = (\emptyset_{90\%} - \emptyset_{10\%}) / ((\emptyset_{90\%} + \emptyset_{10\%})/2)$$

in which $F_{90\%}$ is the distribution factor at 80%;

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

Specific examples of such compositions are disclosed in the following Tables.

TABLE A

Example of composition of dispersible tablets for oral administration containing compound of Formula II and compound of Formula I as active agents.

| | |
|---|---|
| Nitazoxanide (99%) + desacetyl-nitazoxanide (1%) | 200 mg |
| Microcrystalline cellulose | 116 mg |
| Avicel pH 102 sold by FMC-USA | |
| Crospovidone | 25 mg |
| Magnesium stearate | 3 mg |
| Colloidal silicon dioxide | 5 mg |
| Citric acid | 10 mg |
| Strawberry flavor No. 877720 sold by Robertet | 10 mg |
| Sodium saccharinate | 2 mg |

TABLE B

Example of composition of coated tablets for oral administration containing compound of Formula II and compound of Formula I as active agents.

| | |
|---|---|
| Nitazoxanide | 500 mg |
| Maize starch | 60 mg |
| Pregelatinized Maize starch | 70 mg |
| Hydroxypropyl methylcellulose | 5 mg |
| Sucrose | 20 mg |
| Sodium starch glycollate | 30 mg |
| Citric acid | 25 mg |
| Talc | 8 mg |
| Magnesium stearate | 7 mg |

Coatings:
Hot sugar solution or a film coating being sprayed on the tablets or granules containing 500 mg active agent.

TABLE C

Example of an aqueous suspension for oral administration containing compound of Formula II and compound of Formula I as active agents. The pH of the suspension was about 4.1.

| | |
|---|---|
| Nitazoxanide (98%) + desacetyl-Nitazoxanide (2%) | 2 g |
| Distilled water | 100 ml |
| Sodium benzoate | 0.2 g |
| Saccharose | 30.5 g |
| Xanthan gum | 0.2 g |
| Microcrystalline cellulose and carboxymethylcellulose sodium | 0.8 g |
| Avicel RC-591 sold by FMC - USA | |
| Citric acid | 0.2 g |
| Dihydrated sodium citrate | 50 mg |
| Strawberry flavor No. 877720 sold by Robertet | 125 mg |
| Red dye No. 33 D and C | 1 mg |

TABLE D

Example of a paste for oral administration containing compound of Formula II and compound of Formula I as active agents.

| | |
|---|---|
| Nitazoxanide (98%) + desacetyl-Nitazoxanide (2%) | 500 mg |
| Mineral oil | 10 g |
| Brown sugar | 1 g |
| Microcrystalline cellulose and carboxymethycellulose sodium | 0.8 g |
| Avicel RC-591 sold by FMC | |
| Citric acid | 0.2 g |

TABLE E

Example of a paste or ointment formulation for intravaginal or topical application, said paste or ointment containing compound of Formula II and compound of Formula I as active agents.

| | |
|---|---|
| Nitazoxanide (98%) + desacetyl-Nitazoxanide (2%) | 8 g |
| Cremaphor A6 | 2 g |
| Cremaphor A25 | 1.5 g |
| Mineral oil | 7 g |
| Luvitol EHO | 7 g |
| Glycerol monoester | 4 g |
| Cetylic alcohol | 3 g |
| Simeticone | 0.5 g |
| Germaben II | 1 g |
| Propyleneglycol | 3.5 g |
| Distilled water | 62.5 g |

The pharmaceutical compositions of the invention are compositions having a broad spectrum of action on parasites, bacteria, fungi and viruses, especially when administered orally.

The compositions can contain excipients known as such for the purpose of preparing forms suitable for oral administration.

The compositions contain advantageously a wetting agent and possibly a starch derivative such as those disclosed in U.S. Pat. No. 5,578,621, the content of which is incorporated herein by reference for disclosing possible wetting agents and starch derivatives. The wetting agent as described in U.S. Pat. No. 5,578,621 serves as a dispersing agent.

The efficacy and the safety of the pharmaceutical compositions disclosed hereabove were excellent in animals and in humans. Specifically, in human clinical studies, it has been observed that the efficacy of the pharmaceutical compositions described hereabove are significantly more effective in treating parasitic infections than the same formulations using active compound having particle sizes between 170 and 520 $\mu$m (mean particle size=352 $\mu$m), even when the larger sized particles were administered to patients at doses up to three times higher and for longer periods of time. Examples of cure rates obtained are shown below in Table D.

For each of the parasites listed in Table F, the proportional cure rates were significantly better for the patients treated with active particles between 5 and 200 $\mu$m than for those treated with active particles ranging from 170 $\mu$m to 520 $\mu$m in size, with a statistical significance in each case being p<0.02 (using a standard $X^2$ test). This was the case even through the doses of the larger particle size active agent were usually higher and the duration of treatment was often longer than that administered to the patients receiving pharmaceutical compositions of active agent having particle sizes smaller than 200 $\mu$m. There were no serious adverse effects reported for either group of patients.

Results similar to those described above for human studies have also been observed in animal testing.

In addition, the adverse reactions observed in dogs after oral administration of a single dose of 50 milligrams per kilogram of compound of Formula I and compound of Formula II have not been observed in extensive studies in animals using compound of Formula I and compound of Formula II have a particle size between 5 and 200 $\mu$m (mean>10 $\mu$m), even when the same dose or a higher dose of the compounds were administered daily for 90 days or longer.

Moreover, said compositions were stable (even when subjected to temperatures of 40° C. and 65% relative humidity for six months or, in the case of liquid suspensions, when suspended in water under these conditions for 3 months) thereby assuring that the active ingredients do not degrade and that the compositions maintain their efficacy for a period of time after their preparation which is suitable for medicinal and commercial purposes.

It is obvious that the composition of the invention may contain further active agents, for example in the form of solid particles.

What I claim is:

1. A pharmaceutical composition for oral administration containing as active agent, an effective amount of solid particles having a particle size smaller than 200 $\mu$m of a compound of formula II

TABLE F

Comparison of results of human clinical studies using compounds of Formula I and Formula II having particle sizes ranging from 170 $\mu$m to 520 $\mu$m (mean = 352 $\mu$m) with results obtained using Formula I and Formula II having particle sizes ranging from 5 $\mu$m to 200 $\mu$m (mean = 34 $\mu$m).

| | Compound of Formula I (98%) + Compound of Formula II (2%) | |
|---|---|---|
| Parasite | Particle sizes 170 to 520 $\mu$m<br>Dose = 15 to 50 mg/kg/day for 3 to 7 days<br>No. Cured/Total = % Cure Rate | Particle sizes 5 to 200 $\mu$m<br>Dose = 15 mg/kg/day for days<br>No. Cured/Total = % Cure Rate |
| *Blastocystis hominis* | 12/27 = 44% | 10/10 = 100% |
| *Entamoeba histolytica* | 29/47 = 62% | 106/133 = 80% |
| *Giardia lamblia* | 11/37 = 30% | 50/73 = 68% |
| *Ascaris lumbricoides* | 3/69 = 4% | 144/179 = 80% |
| *Trichuris trichiura* | 7/48 = 15% | 58/79 = 73% |

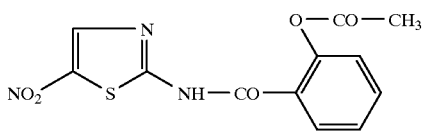

in which the mean particle size of the said active solid particles is greater than 10 μm.

2. The composition of claim 1, in which the mean particle size of the said active solid particles is between 10 and 100 μm.

3. The composition of claim 1, in which the mean particle size of the said active solid particles is between 20 and 50 μm.

4. The composition of claim 1, in which less than 10% of the said active solid particles has a particle size larger than 100 μm.

5. The composition of claim 1, in which at least 50% of the said active solid particles has a particle size smaller than 50 μm.

6. The composition of claim 1, in which less than 10% of the said active solid particles has a particle size smaller than 5 μm.

7. The composition of claim 1 in which the distribution factor of the said active solid particles is between 0.8 and 2, said distribution factor being calculated by the following formula:

$$F_{90\%} = (\emptyset_{90\%} - \emptyset_{10\%})/((\emptyset_{90\%} + \emptyset_{10\%})/2)$$

in which $F_{90\%}$ is the distribution factor at 90%;

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

8. The composition of claim 1, in which the distribution factor of the said active solid particles is between 1.1 and 1.9, said distribution factor being calculated by the following formula $$F_{90\%} = (\emptyset_{90\%} - \emptyset_{10\%})/((\emptyset_{90\%} + \emptyset_{10}\%)/2)$$

in which $F_{90\%}$ is the distribution factor at 90%

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

9. The composition of claim 1, which comprises at least one pharmaceutically acceptable acid.

10. The composition of claim 1, which comprises at least one pharmaceutically acceptable acid selected from the group consisting of citric acid, glutamic acid, succinic acid, ethanesulfonic acid, acetic acid, tartric acid, ascorbic acid, methanesulfonic acid, fumaric acid, adipic acid, malic acid and mixtures thereof.

11. The composition of claim 10, in which the ratio of the weight of pharmaceutically acceptable acid/the weight of said active solid particles is between 0.01 and 0.5

12. The composition of claim 10, in which the ratio of the weight of pharmaceutically acceptable acid/the weight of said active solid particles is between 0.03 and 0.2.

13. A pharmaceutical composition for oral administration containing:

as active agent, an effective amount of solid particles having a particle size smaller than 200 μm of a compound of formula II

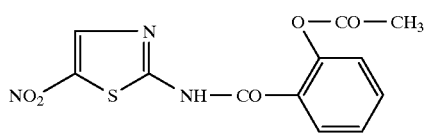

in which the mean particle size of the said active solid particles is greater than 10 μm; and at least one granulating agent.

14. The composition of claim 13, in which the mean particle size of the said active solid particles is comprised between 10 and 100 μm.

15. The composition of claim 13, in which the mean particle size of the said active solid particles is comprised between 20 and 50 μm.

16. The composition of claim 13, in which less than 10% of the said active solid particles has a particle size larger than 100 μm.

17. The composition of claim 13, in which at least 50% of the said active solid particles has a particle size smaller than 50 μm.

18. The composition of claim 13, in which less than 10% of the said active solid particles has a particle size smaller than 5 μm.

19. The composition of claim 13, in which the granulated active solid particles contains from 2 to 99.97% by weight of the said active compound and from 0.03 to 10% by weight of a granulating agent.

20. The composition of claim 19, in which the granulating agent is selected from the group consisting of polyvinylpyrrolidone, water, alcohol, sucrose hydroxyl cellulose and mixture thereof.

21. The composition of claim 13, in which the granulated active solid particles contain at least one pharmaceutically acceptable acid.

22. The composition of claim 13, in which the granulated active solid particles contain at least one pharmaceutically acceptable acid selected from the group consisting of citric acid, glutamic acid, succinic acid, ethanesulfonic acid, acetic acid, tartric acid, ascorbic acid, methanesulfonic acid, fumaric acid, adipic acid, malic acid and mixtures thereof.

23. The composition of claim 22, in which, for the granulated active solid particles, the ratio of the weight of pharmaceutically acceptable acid/the weight of said active agent is between 0.01 and 0.5.

24. A solid dosage form for oral administration containing:

as active agent, an effective amount of solid particles having a particle size smaller than 200 μm of a compound of formula II

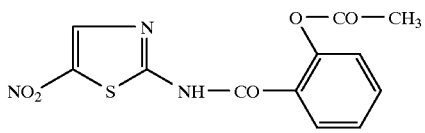

in which the mean particle size of the said active solid particles is greater than 10 μm;

at least one wetting agent, and at least one starch derivative.

25. The dosage form of claim 24, in which the mean particle size of the said active solid particles is between 10 and 100 μm.

26. The dosage form of claim 24, in which the mean particle size of the said active solid particles is between 20 and 50 μm.

27. The dosage form of claim 24, in which less than 10% of the said active solid particles has a particle size larger than 100 μm.

28. The dosage form of claim 24, in which at least 50% of the said active solid particles has a particle size smaller than 50 μm.

29. The dosage form of claim 24, in which less than 10% of the said active solid particles has a particle size smaller than 5 μm.

30. The composition of claim 24, in which the distribution factor of the said active solid particles is between 0.8 and 2, said distribution factor begin calculated by the following formula:

$$F_{90\%} = (\emptyset_{90\%} - \emptyset_{10\%})/((\emptyset_{90\%} + \emptyset_{10\%})/2)$$

in which $F_{90\%}$ is the distribution factor at 90%;

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

31. The composition of claim 24, in which the distribution factor of the said active solid particles is between 1.1 and 1.9, said distribution factor being calculated by the following formula $$F_{90\%} = (\emptyset_{90\%} - \emptyset_{10\%})/((\emptyset_{90\%} + \emptyset_{10\%})/2)$$

in which $F_{90\%}$ is the distribution factor at 90%;

$\emptyset_{90\%}$ is the maximum particle size of the fraction of particles corresponding to 90% of the said active solid particles, and $\emptyset_{10\%}$ is the maximum particle size of the fraction of particles corresponding to 10% of the said active solid particles.

32. The dosage form of claim 24, which includes particles of at least one pharmaceutically acceptable acid.

33. The dosage form of claim 24, in which the active particles are granulated, said granulated active agent containing form 2 to 99.97% by weight of the said active compound and from 0.03 to 10% by weight of a granulating agent.

34. The dosage form of claim 33, in which the granulating agent is selected from the group consisting of polyvinylpyrrolidone, water, alcohol, sucrose hydroxyl cellulose and mixture thereof.

35. The dosage form of claim 24, said form comprised of:

solid granulated active particles, said granulated active particles containing from 2 to 90% by weigh of the said active compound, from 0.03 to 10% by weight of a granulating agent, and at least one pharmaceutically acceptable acid;

at least one wetting agent;

at least one starch derivative, and at least one pharmaceutically acceptable acid.

36. An aqueous or other liquid suspension of solid particles for oral administration, said suspension containing:

as active agent, an effective amount of solid particles having a particle size smaller than 200 μm of a compound of formula II

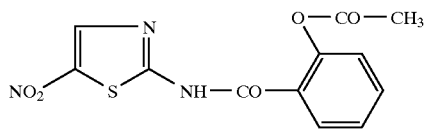

in which the mean particle size of the said active solid particles is greater than 10 μm; and at least one pharmaceutically acceptable acid, the pH of the suspension being between 2 and 6.

37. The suspension of claim 36, in which the pH of the suspension is between 3 and 5.

38. An aqueous or other liquid suspension of solid particles for oral administration, said suspension containing:

as active agent, an effective amount of solid particles having a particle size smaller than 200 μm of a compound of formula II

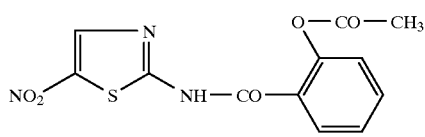

in which the mean particle size of the said active solid particles is greater than 10 μm;

a granulating agent; and at least one pharmaceutically acceptable acid, the pH of the suspension being between 2 and 6.

39. The suspension of claim 38, in which the pH of the suspension is between 3 and 5.

40. A pharmaceutical composition for oral administration containing:

as active agent, an effective amount of solid particles having a particle size smaller than 200 μm of a compound of formula II

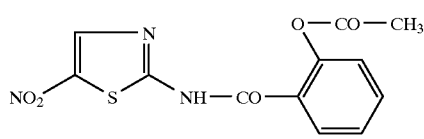

in which the mean particle size of the said active solid particles is greater than 10 μm;

at least one pharmaceutically acceptable acid.

41. A paste for oral administration containing:

as active agent, an effective amount of solid particles having a particle size smaller than 200 μm of a compound of formula II

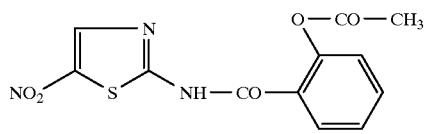

in which the mean particle size of the said active solid particles is greater than 10 μm;

at least one wetting agent;

at least one pharmaceutically acceptable acid, the pH of the paste being between 2 and 6;

at least one thickener.

42. The paste of claim 41, in which the thickener is selected from the group consisting of Xanthan gum, a guar gum, crystalline cellulose, carruba gum, carboxymethylcellulose or a mixture thereof.

43. A paste for topical administration containing:

as active agent, an effective amount of solid particles having a particle size smaller than 200 μm of a compound of formula II

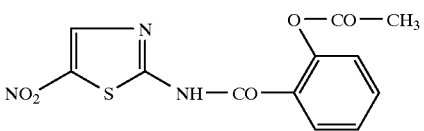

in which the mean particle size of the said active solid particles is greater than 10 μm;

at least one wetting agent;

at least one additive selected from the group consisting of cetylic alcohol, glyceride derivatives, propyleneglycol and mixtures thereof;

at least one thickener.

44. A paste for intravaginal administration containing:

as active agent, solid particles having a particle size smaller than 200 μm of a compound of formula II

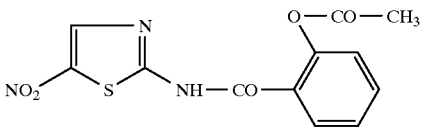

in which the mean particle size of the said active solid particles is greater than 10 μm;

at least one wetting agent;

at least one additive selected from the group consisting of cetylic alcohol, glyceride derivatives, propyleneglycol and mixtures thereof;

at least one thickener.

* * * * *